United States Patent
Hörlin (12)

(10) Patent No.: US 6,470,884 B2
(45) Date of Patent: Oct. 29, 2002

(54) CAPSULE OPENING ARRANGEMENT FOR USE IN A POWDER INHALER

(75) Inventor: Ernst Hörlin, Askim (SE)

(73) Assignee: Aventis Pharma Limited, Kent (GB)

( * ) Notice: Subject to any disclaimer, the term of this patent is extended or adjusted under 35 U.S.C. 154(b) by 0 days.

(21) Appl. No.: 09/834,932

(22) Filed: Apr. 16, 2001

(65) Prior Publication Data
US 2001/0020472 A1 Sep. 13, 2001

Related U.S. Application Data

(63) Continuation of application No. 09/117,385, filed as application No. PCT/SE97/00120 on Jan. 27, 1997, now abandoned.

(30) Foreign Application Priority Data

Jan. 29, 1996 (SE) ................................................ 9600306

(51) Int. Cl.$^7$ ................................................ B65D 83/06
(52) U.S. Cl. ........................... 128/203.15; 128/203.23; 128/203.21; 604/58
(58) Field of Search ................... 128/200.14, 200.24, 128/203.12–203.15, 203.21, 203.23; 604/57, 58

(56) References Cited

U.S. PATENT DOCUMENTS

| 3,918,451 A | | 11/1975 | Steil |
| 4,013,075 A | * | 3/1977 | Cocozza ............... 128/203.15 |
| 4,069,819 A | | 1/1978 | Valentini et al. |
| 4,117,844 A | | 10/1978 | James |
| 4,210,140 A | | 7/1980 | James et al. |
| 4,446,862 A | | 5/1984 | Baum et al. |
| 4,860,740 A | | 8/1989 | Kirk et al. |
| 5,372,128 A | | 12/1994 | Haber et al. |
| 5,651,359 A | | 7/1997 | Bougamont et al. |
| 5,673,686 A | | 10/1997 | Villax et al. |
| 5,921,237 A | | 7/1999 | Eisele et al. |
| 5,947,118 A | | 9/1999 | Hochrainer et al. |

FOREIGN PATENT DOCUMENTS

| DE | 2408791 | 2/1973 |
| EP | 0707862 | 4/1996 |
| HU | 171644 | 9/1978 |
| HU | 174930 | 9/1980 |
| HU | 205721 | 6/1992 |
| HU | 217896 | 5/2000 |
| WO | 9119524 | 12/1991 |
| WO | 9503846 | 2/1995 |

* cited by examiner

Primary Examiner—Glenn K. Dawson
(74) Attorney, Agent, or Firm—Birch, Stewart, Kolasch & Birch, LLP

(57) ABSTRACT

The invention relates to a capsule opening arrangement for a powder inhaler device. The arrangement has a first part and a second part which are relatively movable with respect to one another. The first part has a capsule support including an aperture for supporting at least one severable capsule. The second part contains a capsule severing device fixedly located therein so as to pass across the supporting aperture during relative movement of the first and second parts. The opening arrangement provides particular advantages in that the capsule, after severing, has a large open area from which powder can be extracted without any part of the capsule interfering with the powder flow.

15 Claims, 6 Drawing Sheets

CAPSULE OPENING ARRANGEMENT FOR USE IN A POWDER INHALER

This application is a continuation of application Ser. No 09/117,385, filed on Sep. 21, 1998, now ABN for which priority is claimed under 35 U.S.C. § 120. Application Ser. No. 09/117,385 is the national phase of PCT International Application No. PCT/SE97/00120 filed on Jan. 27, 1997 under 35 U.S.C. § 371. The entire contents of each of the above-identified applications are hereby incorporated by reference. This application also claims priority of application Ser. No. 9600306-6 filed in Sweden on Jan. 29, 1996 under 35 U.S.C. § 119.

FIELD OF THE INVENTION

The invention relates to a capsule opening arrangement for a powder inhaler device according to the preamble of claim 1. In particular, the invention relates to a capsule severing arrangement.

BACKGROUND TO THE INVENTION

Several types of powder inhaler devices are known in the prior art. One of these types is a device which uses capsules containing powder, said capsules needing to be opened before the device can be operated by a user.

Two main types of device are available for opening such capsules. The first is a pin arrangement within the inhaler device, said pin being operable so as to pierce a capsule and thus allow access to its contents. Such a device is known from U.S. Pat. No. 4 069 819 for example. Due to the presence of a reduced pressure around the powder capsule when a user inhales, and due to a processional motion of the capsule in a restricted cavity, the powder is withdrawn therefrom.

The second type of device for opening such capsules is a device which separates a two-part capsule into its two parts by first clamping one part and then forcing the other part away therefrom. An example of such a device is disclosed in WO-A-91/19524, said device corresponding to the features defined in the preamble of claim 1.

Such devices suffer from several disadvantages. The pin-piercing device produces a relatively small opening within the capsule and may thus lead to it not being completely emptied. Although the problem can be alleviated to some extent by providing multiple piercing elements, variations in the dose provided may still be observed.

The capsule-separation device relies on the capsule being of the separable type. Additionally, the separation of the capsules relies to a great extent on a good balance between capsule shell hardness and separation force required to separate the two parts. Moreover, even when separation is achieved, the loose parts are left to block the flow passage of the powder. Furthermore a grid structure is also required, on which powder may accumulate and cause blockage.

SUMMARY OF THE PRESENT INVENTION

The present invention seeks to provide a solution to the aforementioned problems by means of a capsule opening arrangement having the features defined in appended claim 1.

Preferred features of the invention are defined in the dependent claims.

In a particularly preferred embodiment of the invention, the opening device is intended to be attached, or integral with, the powder inhaler of the type disclosed in WO-A95/03846. To avoid repetition of the principal of operation of such device, which will be clear to the skilled man upon reading said document, specific reference is hereby made to said document in its entirety.

Although the invention will be elucidated by reference to a particular form of a device of the type according to WOA-95/03846, it will be understood by the skilled man that the capsule opening device of the present invention will also be applicable to other forms of inhaler devices.

BRIEF DESCRIPTION OF THE DRAWINGS

The invention will now be described in more detail with reference to the accompanying drawings, in which.

Detailed description of preferred embodiments

Figure 1:
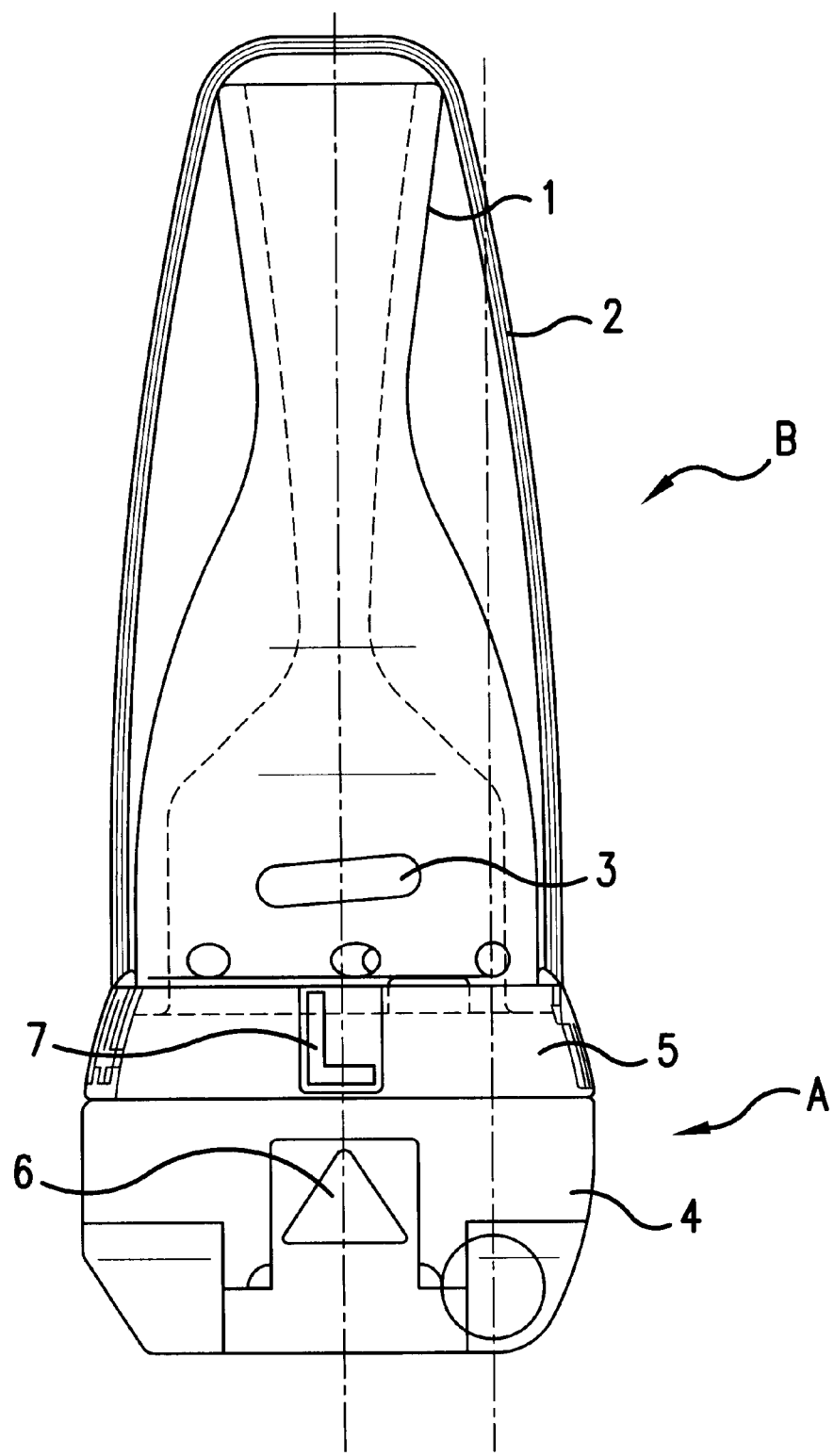
FIG. 1 is a schematic view of a powder inhaler device having an upper and lower section, said lower section containing the capsule opening arrangement of the invention.

The inhaler device depicted in FIG. 1 has a lower section A and an upper section B. The lower section A contains the capsule opening arrangement of the invention, whilst the upper section B contains a united tubular mouthpiece/chamber 1 of the inhaler, sealed by a cover member 2. The cover member is removably attached to the upper mouthpiece/chamber 1 by means of threads 3 for example. Other means of removable attachment may of course be used instead of threads. The thread 3 attachment is shown only schematically in FIG. 1.

The external profile of the mouthpiece, even though hidden by the cover, has been drawn in solid lines in FIG. 1 so as to show a differentiation compared to the inner passageway of said mouthpiece/chamber which is shown in dashed lines. Said mouthpiece/chamber portion corresponds basically to that disclosed in WO-A-95/03846.

The lower section A is divided into first and second parts 4 and 5. The second part 5 is non-rotatably attached to mouthpiece/chamber 1 and first part 4 is rotatably mounted relative to said second part 5. An indicator arrow 6, moulded into part 4, indicates the relative position with respect to an indicator 7 on the second part 5.

In the example to be described, the lower section A contains four capsules. Thus, four markings (and possibly also a further one, "L") are provided around the outer surface of the second part.

Figure 2:
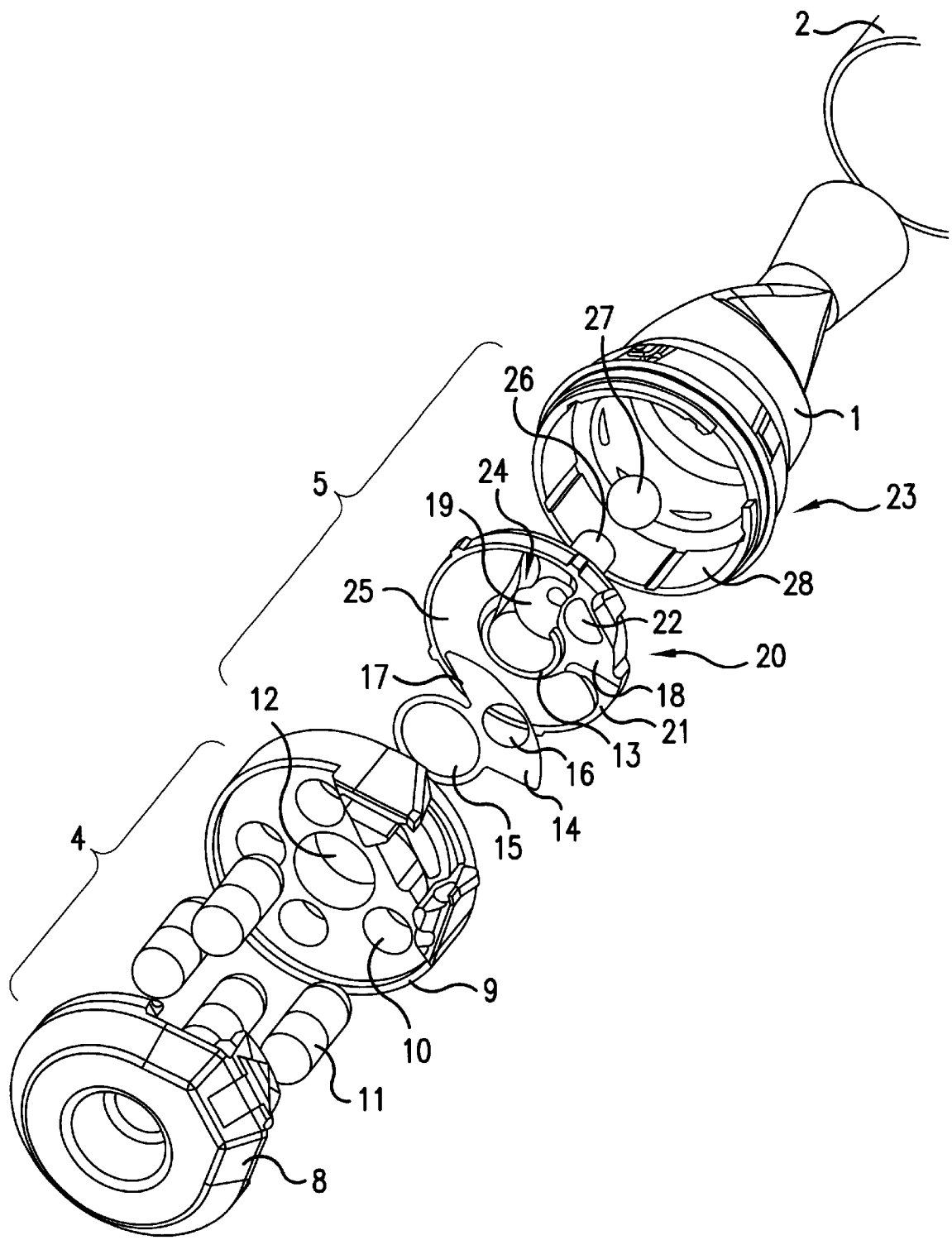
FIG. 2 is an exploded view of the powder inhaler device of FIG. 1, depicting its various component parts.

In the exploded view in FIG. 2, the various structural elements can be seen in more detail. The first part 4 comprises two constituent parts 8 and 9. Part 8 is a cover member for the lower part of the device and serves to maintain the four severable capsules 11 within the other part 9 which is a capsule supporting means. Parts 8 and 9 are preferably hingedly attached to one another.

The capsule supporting means 9 has at least one capsule supporting aperture 10. In the depicted embodiment there are four capsule supporting apertures 10. The apertures 10 are formed such that the capsules may be easily fitted into place within said apertures, without a large amount of play. The capsules 11 may be a press fit into the apertures 10. The capsules 11 are normally made of relatively flexible material such as a gelatine compound (known per se) and may typically contain between 5 mg and 40 mg of powder substance to be inhaled, although such amounts are not limiting for the invention.

Figure 3:
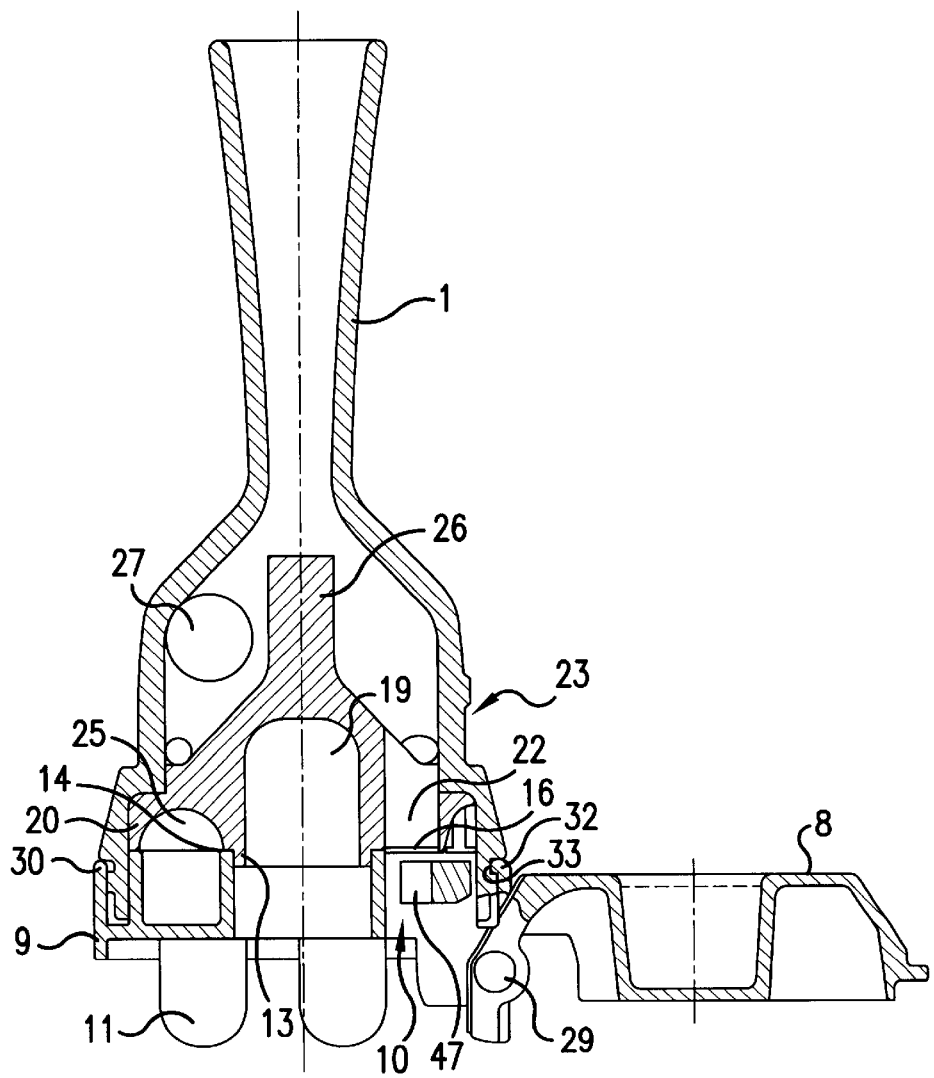
FIG. 3 is a cross-sectional view through the central rotational axis of the device, in which the cover of the capsule opening device has been opened.

In the centre of the part 9 there is an aperture 12. This aperture 12 fits around a projection 13 on the second part 5 when the device is ready for use. This fitted relationship is shown in FIG. 3.

Second part 5 is comprised of three pieces fitted together. The first piece is a severing means in the form of a flat knife blade 14 having a severing edge 17. The second piece is a knife blade support means 20, and the third piece a chamber section 23 united with the mouthpiece (either integrally or by attachment of said parts).

The knife blade 14 has a two apertures therethrough. The first aperture 15 is formed by a substantially annular portion 45. Said portion 45 fits, preferably as a push-fit, around the partially annular, projecting portion 13 of said blade support means 20.

The blade support means 20 has a surface 18 formed therein which is recessed with respect to the lower planar surface 21 of said support means 20 by the thickness of said knife blade 14. The knife blade is thus supported in position by two means and its lower surface is flush with the planar surface(s) 46 outside the recess.

The second aperture 16 in the knife blade 14 is positioned in line with a powder exit passageway 22 which passes from the lower side of said blade support means 20 to the upper side (i.e. the chamber side) thereof. It should be understood that the expression "in line with" is intended here to mean that the aperture 16 and the passageway 22 are in direct communication with one another. However the aperture 16 and the passageway 22 inlet do not need to be the same shape or size, and indeed will often be different (see e.g. the arrangement shown in FIG. 8). The exact shape and/or size will depend on the design chosen.

Figure 7:
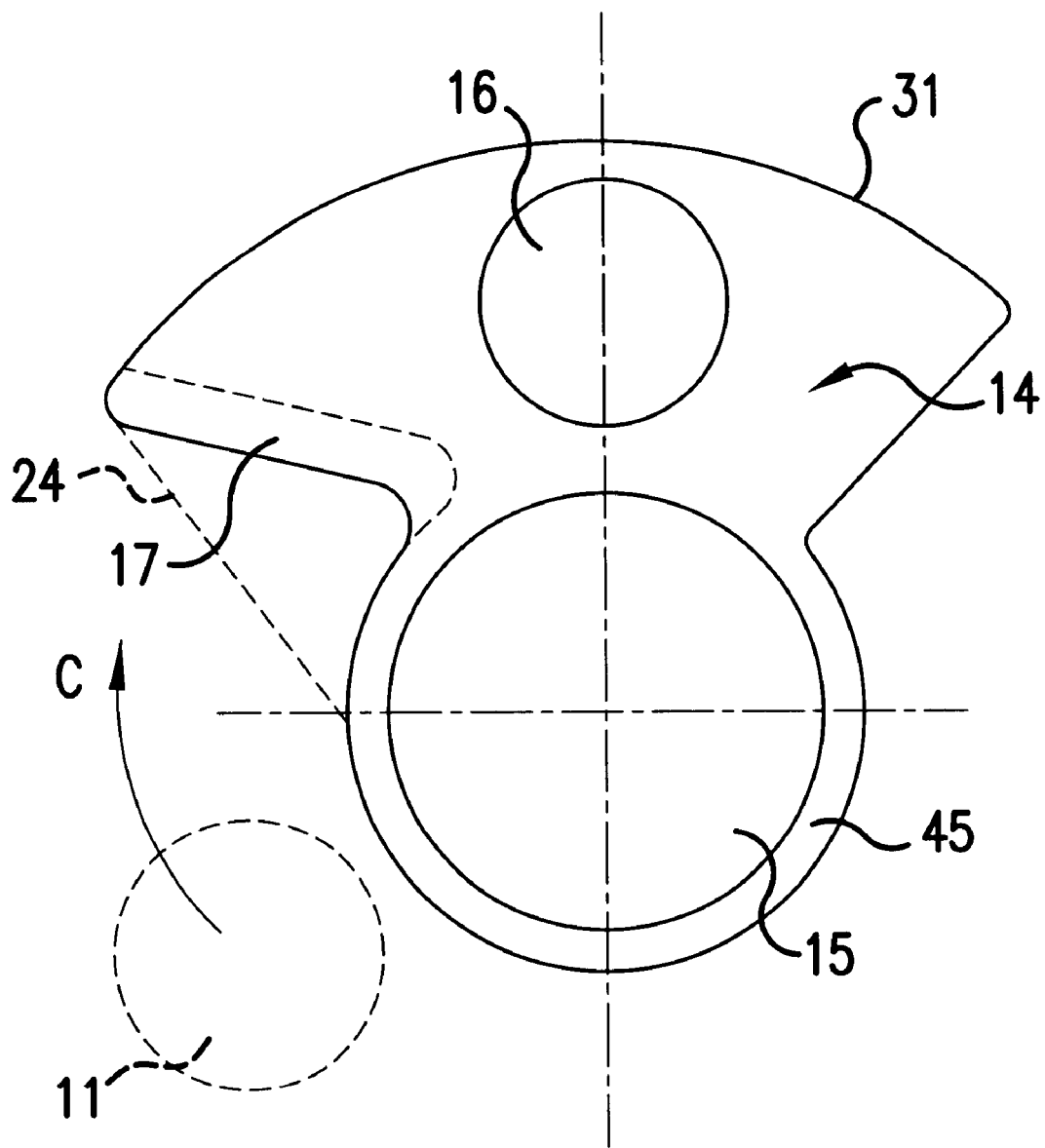
FIG. 7 depicts an enlarged view of the severing means of the capsule opening device together with indications showing superimposed capsule movement and the edge of the entrance to the capsule receiving cavity.

The blade 14 is shown in larger detail in FIG. 7. The outside of the knife blade is preferably in the form of a circular arc 31 and fits closely to the circular inner wall perimeter of blade support means 20.

The blade support means 20 comprises a receiving cavity 19 for receiving portions of said capsules 11 which are severed by knife edge 17. A large portion of said cavity 19 is positioned above said knife blade 14. With the knife blade 14 in place (not shown in FIG. 2), the receiving cavity 19 has a single entrance 24 extending on one side of said cutting edge 17 (i.e. to the anti-clockwise side as seen in the view in FIG. 2). The position of said entrance is also shown in FIG. 7.

The blade support means 20 further comprises a capsule end guide channel 25 allowing sliding contact with the ends of each of said capsules during their rotational indexed movement. One end of said guide channel 25 also forms the single entrance 24 of the receiving cavity 19.

On the chamber side of the blade support means 20 there is a central projecting member 26 which fits into the chamber 35 (see e.g. FIG. 5) to create a flow restriction between the chamber and the mouthpiece (see also WO-A-91/19524). A freely movable element 27 is also contained therein (see WO-A-91/19524).

Part 20 is attached to part 23 so that no relative movement between said parts occurs during normal use. However, part 9 is attached so as to be rotatably received at its outer edge within the lower part of the wall portion 28 of part 23. As shown in FIG. 3, this is achieved by a radially inwardly projecting portion 32 engaging (e.g. as a snap-fit) into a groove 33 in part 23.

Figure 4:
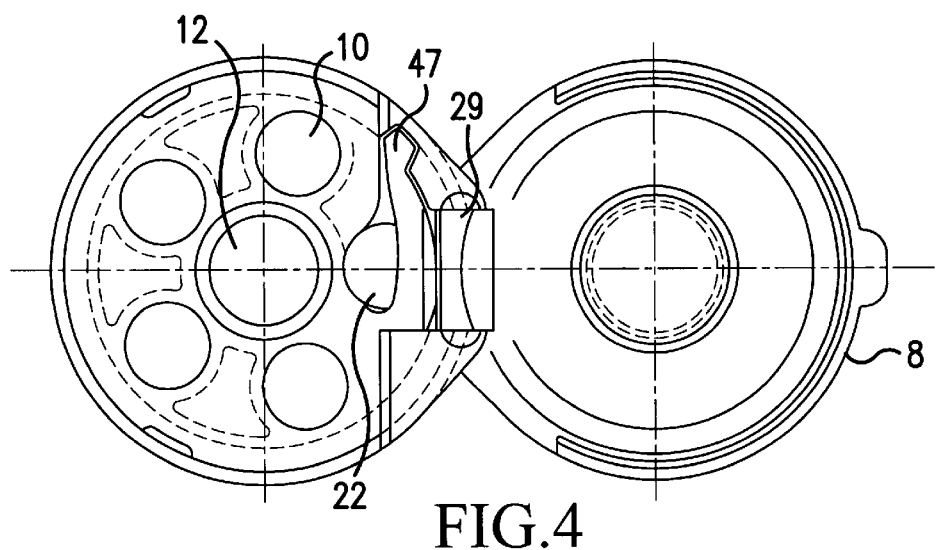
FIG. 4 is an end view on to the base of the device depicted in FIG. 3.

FIG. 4 shows an end view of said inhaler from the lower end. Here it can be seen that none of the four capsule support apertures is aligned with the passageway 22. An indexed rotation of about 72° is required for such alignment between one aperture 10 and said passageway in the depicted embodiment, presuming the apertures to be equally angularly spaced.

Part 9 is arranged to be rotatably indexed between various positions, so that opened capsules will assume an indexed position aligned with the powder exit passageway 22. In order to accomplish this, an indexing means is provided between part 9 and part 20/23. Such an indexing means is shown in FIGS. 3 and 4 by element 47 which is a sprung arm which can be moved out of its detent position by a sufficient rotational force in a rotational direction towards knife edge 17 applied between parts 9 and 5.

Figure 5:
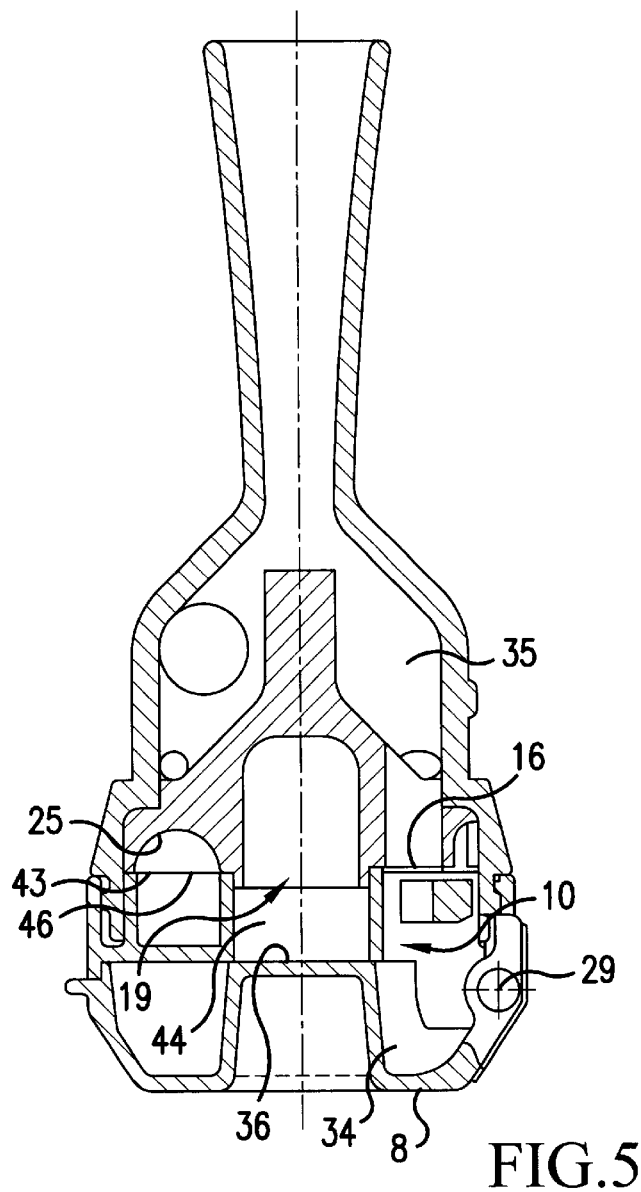
FIG. 5 is a view similar to FIG. 3 but with the cover closed.
Figure 6:
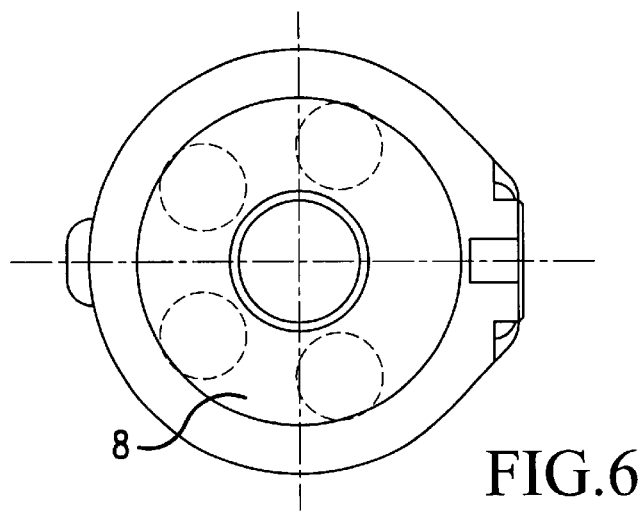
FIG. 6 is an end view on to the base of the cover depicted in FIG. 5.

FIGS. 5 and 6 show the inhaler according to FIGS. 3 and 4, with the lower cap in a closed state. In the bottom of the cap are semi-spherical recesses 34 which align with capsule support apertures 10. Together with channel 25, these elements 10 and 34 form the supporting and guiding elements for said capsules.

In FIG. 5, a severed capsule (not shown) will be positioned within the space bounded by the lower edge of the blade aperture 16 and the recess 34. In this manner a direct flow communication is established between chamber 35 and the inside of a severed capsule (not shown in FIG. 5). FIG. 6 shows an end view of the lower part 8 in FIG. 5.

FIG. 7 shows an enlarged view, from below, of the knife blade 14 depicted in FIG. 1. The size, and even the shape, of the apertures 15 and 16 may vary according to circumstances, although generally the internal diameter of aperture 15 will be a push-fit with respect to the outer periphery of projection 13. Although the knife is preferably made of steel and the rest of the inhaler of plastics, the knife may also be made of plastics.

FIG. 7 also schematically shows a horizontal section through capsule 11 by means of dotted lines. The capsule moves in a circular arc as indicated by arrow C (by rotational movement of part 9 having apertures 10) towards the knife edge 17. The capsule will start from a first indexed position in which it is temporarily held upstream of the knife edge by some blocking or detent means (e.g. a ratchet or the like). Upon forward movement and upon reaching the knife edge, it will be pierced. Continued movement of the capsule in the direction of arrow C will result in the top thereof being cut off (severed) and moving into the entrance 24 of the receiving cavity 19. Still further movement of the capsule will allow the severed capsule to reach its second indexed position directly below the aperture 16. In this position, the powder contents of the capsule will then be in direct communication with passageway 22 and can be withdrawn by sucking through mouthpiece 1.

During movement of the capsule 11, which is supported in aperture 10 of part 9, the upper, generally planar, surface 43 of said part 9 will be in sliding contact with the lower surface of the knife 14 and the surface 46 with which it is flush. In this way, the severed capsule remaining in the part 9 will have its upper severed surface also in sliding contact with the lower surface of knife 14 and thus will form a relatively good seal between the two parts. This seal will help ensure that the reduced pressure in chamber 35 will efficiently withdraw the powder from the severed capsule.

The upper parts of the capsule 11 which enter into the cavity 19 via entrance 24 are held in the cavity which is bounded partly by the knife blade upper surface and surface 36 of cover 8 (see FIG. 5) and also the upper planar surface of part 9. Since the entrance 24 is always sealed by the upper planar surface of part 9 (apart from when actually severing a capsule), no capsule parts can fall out and block the device. Removal of said capsule parts is effected only by opening lower end cap 8 which move from cavity 19, through an open space 44 in the middle of part 9 and to the outside of the device.

When operating the device as described above, the inhaler should be kept upright as shown in e.g. FIG. 5. Otherwise there is a risk of powder exiting the capsule prematurely and ending up in the cavity 19.

Figure 8:
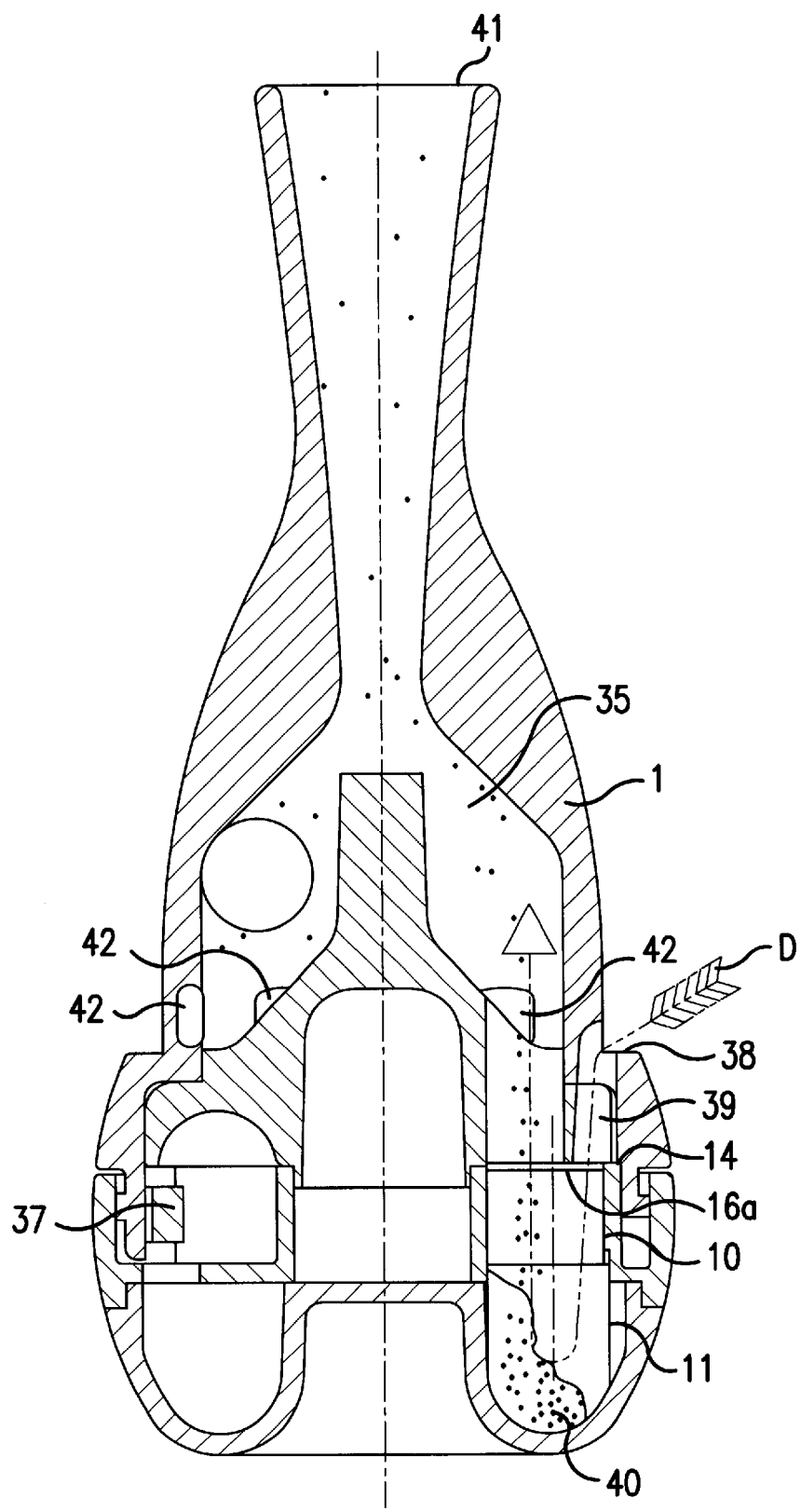
FIG. 8 depicts a cross-sectional view of a further embodiment of the device, similar to the view in FIG. 5, but with a severed capsule in place and being provided with an airflow passageway which eases capsule-emptying.

In the further embodiment of the invention shown in FIG. 8, which corresponds in most aspects to FIG. 5, an air passageway 39 from the surroundings is arranged in said mouthpiece/chamber portion 1 and in said second portion 9.

An air passageway is thus formed from the surroundings, directly through said mouthpiece/chamber portion and said second part 9, as well as through said aperture 16a in the knife 14. The passageway 39 is thus in communication with said aperture 10 (or a severed capsule 11 if one is present). The aperture 16a will thus be larger, or of a different shape, compared to aperture 16 in FIG. 5, all other things being equal.

When a suction force is applied to the open end 41 of mouthpiece 1, air will be sucked through apertures 42 into the chamber to create the required swirling effect (see WOA-95/03846). Similarly, air will also be drawn in through passageway 39, and will impinge onto the powder 40 within the severed capsule 11 and draw it along with the flow into the swirling air in chamber 35. In this way, emptying of the capsule is facilitated to a greater degree compared to the arrangement shown in FIG. 5.

The passageway 39 is preferably arranged so that its longitudinal axis is directed to a point impinging onto the passageway-side of the capsule, as shown in FIG. 8. In this way all the air will tend to act in one direction when moving through the capsule, rather than merely creating counteractive turbulence within the capsule, as would be the case if the passageway were directed to the other side of the capsule 11.

As will be clear from the a foregoing, the provision of an air passageway, as described, for emptying a severed capsule in an inhaler device, is an aspect of the invention which can be used independently of the exact type of opening means used, as long as an opened upright capsule will be presented for use. Its subject matter, in the broadest sense, may thus form an independent invention.

However its use with the arrangement of the present invention is particularly preferred.

Similarly, the provision of the particular severed capsule receiving cavity, in its broadest sense, by which severed portions of capsules are removed from interference with the airstream or powder stream flow in inhaler devices, is an aspect of the invention which can be the subject matter of an independent invention. Its use in the arrangement of the present invention is however preferred.

An indexing detent means 37 is shown on one side of the capsule opening means. Said detent means may be of any suitable type, several of which are known to the skilled man and which therefore do not need to be described in more detail.

Radially outwardly of the inlet to the passageway 39 is a ledge 38. Said ledge 38 is so arranged such that when a cover 2 (as in FIG. 1) is fitted over the mouthpiece 1, the inner surface of said cover 2 will seal the passageway 39 from the surroundings.

Although the invention has been described above with reference to particular embodiments of the invention depicted in the drawings, it is to be understood that such embodiments are not limiting for the invention, the scope of which is defined by the following claims.

For example, the type of capsule used does not need to be a two-part capsule, but may be any other type of severable capsule. Similarly, whilst the capsule has been shown as being generally oval and having two parts of different outer diameter attached to each other, other shapes of capsule may be used.

I claim:

1. A capsule opening arrangement for a powder inhaler device, comprising:
   a first part and second part, said first part and said second part being relatively movable with respect to one another,
   wherein said first part has a capsule supporting means comprising an aperture for supporting at least one severable capsule, and said second part is fitted with a capsule severing means fixedly located in said second part so as to pass across said supporting aperture during relative movement of said first and second parts,
   wherein said first part has a cover member serving the function of maintaining at least one severable capsule, which may be inserted into said device, within said capsule supporting means, said cover member being movable relative to said second part.

2. The capsule opening arrangement according to claim 1, wherein said severing means is positioned at only one end of said supporting aperture.

3. The capsule opening arrangement according to claim 1, wherein said capsule supporting means is arranged to rotate between at least first and second indexed positions, and said aperture of said capsule supporting means is located ahead of a severing edge of said severing means in said first indexed position, and wherein in said second indexed position, said aperture is located in communication with a powder exit passageway passing through said second part.

4. The capsule opening arrangement according to claim 3, wherein in one of said indexed positions, said capsule supporting aperture is in line with an inlet of a powder exit passageway and an air inlet from the surroundings, and each of said inlets is arranged within, or in a further member which is united with, said second part.

5. The capsule opening arrangement according to claim 1, wherein said first part having said capsule supporting aperture has a planar upper face which is in sliding contact with a planar lower face of said second part.

6. The capsule opening arrangement according to claim 1, wherein said capsule severing means is constituted by a blade having a planar lower surface, and said blade has an aperture therethrough which is aligned with a powder exit passageway passing through said second part.

7. The capsule opening arrangement according to claim 6, wherein said blade is formed with an integral annular portion, which portion is form fitted to an at least partially cylindrical central projection arranged on said second part, and said lower surface of said blade is planar and lies flush with a planar surface of said second part, said central projection extending past said planar surface of said second part, and against which planar surface of said second part an upper surface of said first part is arranged to slidingly rotate.

8. The capsule opening arrangement according to claim 1, further comprising:
   a receiving cavity for receiving one part of severed capsules provided in said second part, wherein the severing means has a cutting edge located directly above a single entrance to said receiving cavity.

9. The capsule opening arrangement according to claim 8, wherein said receiving cavity has an exit path passing through the center of said second part, said exit path being in communication with a hole in said first part, through which hole parts of severed capsules may be removed.

10. The capsule opening arrangement according to claim 1, wherein said first part comprises two portions which are attached together by a hinge, one of said portions being said cover member, said cover member being openable, and the other of said portions having locating means providing rotatable connection of said first and said second parts.

11. The capsule opening arrangement according to claim 1, wherein at least one severable capsule can be supported by the cover member during relative movement of the severable capsule toward said capsule severing means.

12. The capsule opening arrangement according to claim 1, wherein one end of a severed capsule can be supported by said cover member during inhalation of contents of the severed capsule.

13. A powder inhaler device comprising a capsule opening arrangement in accordance with claim 1, and further comprising a tubular mouthpiece member united with a chamber, said chamber having at least one air entrance passageway which is arranged substantially tangentially with respect to said chamber so as to cause air sucked into said chamber to swirl around said chamber, said chamber and the second part being fixedly united with one another.

14. The powder inhaler according to claim 13, wherein said capsule supporting aperture is rotatably indexable between at least a first and a second position, and wherein in said second position, said supporting aperture is positioned in line with an air inlet from the surroundings and an inlet to a powder exit passageway communicating with said chamber, said air inlet from the surroundings being a passageway having a longitudinal axis aligned so as to cause air from the surroundings to flow towards the bottom of a capsule placed within said aperture.

15. The powder inhaler according to claim 13, wherein said chamber has a projecting central portion for extending towards said mouthpiece so as to provide a flow restriction between said chamber and said mouthpiece, and wherein the powder exit passageway through said second part has its orifice at the end of said chamber opposite to said restriction.

* * * * *